United States Patent [19]
Lazarus et al.

[11] Patent Number: 5,515,932
[45] Date of Patent: May 14, 1996

[54] APPARATUS AND METHOD FOR ENVIRONMENTAL SURVEYING FOR CONTAMINANTS IN ALLUVIAL MATERIALS AND BEDROCK FORMATIONS

[75] Inventors: Jay L. Lazarus; Van G. Baehr; Steve Slade, all of Santa Fe, N.M.

[73] Assignee: Venture Probe, Inc., Santa Fe, N.M.

[21] Appl. No.: 360,641

[22] Filed: Dec. 21, 1994

Related U.S. Application Data

[63] Continuation-in-part of Ser. No. 126,907, Sep. 24, 1993, Pat. No. 5,407,019.
[51] Int. Cl.⁶ .................................................. E21B 3/12
[52] U.S. Cl. ................................................ 175/50; 175/71
[58] Field of Search ................................. 175/20, 50, 71, 175/94, 95, 107, 415, 417

[56] References Cited

U.S. PATENT DOCUMENTS

| | | | |
|---|---|---|---|
| 3,899,033 | 8/1975 | Van Huisen | 175/103 X |
| 4,120,368 | 10/1978 | Johansson | 175/94 X |
| 5,407,019 | 4/1995 | Lazarus et al. | 175/50 |

*Primary Examiner*—William P. Neuder
*Attorney, Agent, or Firm*—Sue Z. Shaper; Butler & Binion

[57] ABSTRACT

Apparatus and method for environmental surveying and prospecting for contaminants in alluvial materials and bedrock formations including using a portable pneumatic rotary percussion drilling machine, preferably pneumatic, having a gas circulation fluid to displace drill cuttings, the machine utilizing a perforated rock drill bit and hollow stem drill rod and potentially including means for lifting water and soil samples, a high pressure source of gas for unclogging perforations in the bit and means for driving and removing casing using the percussion driver.

16 Claims, 3 Drawing Sheets

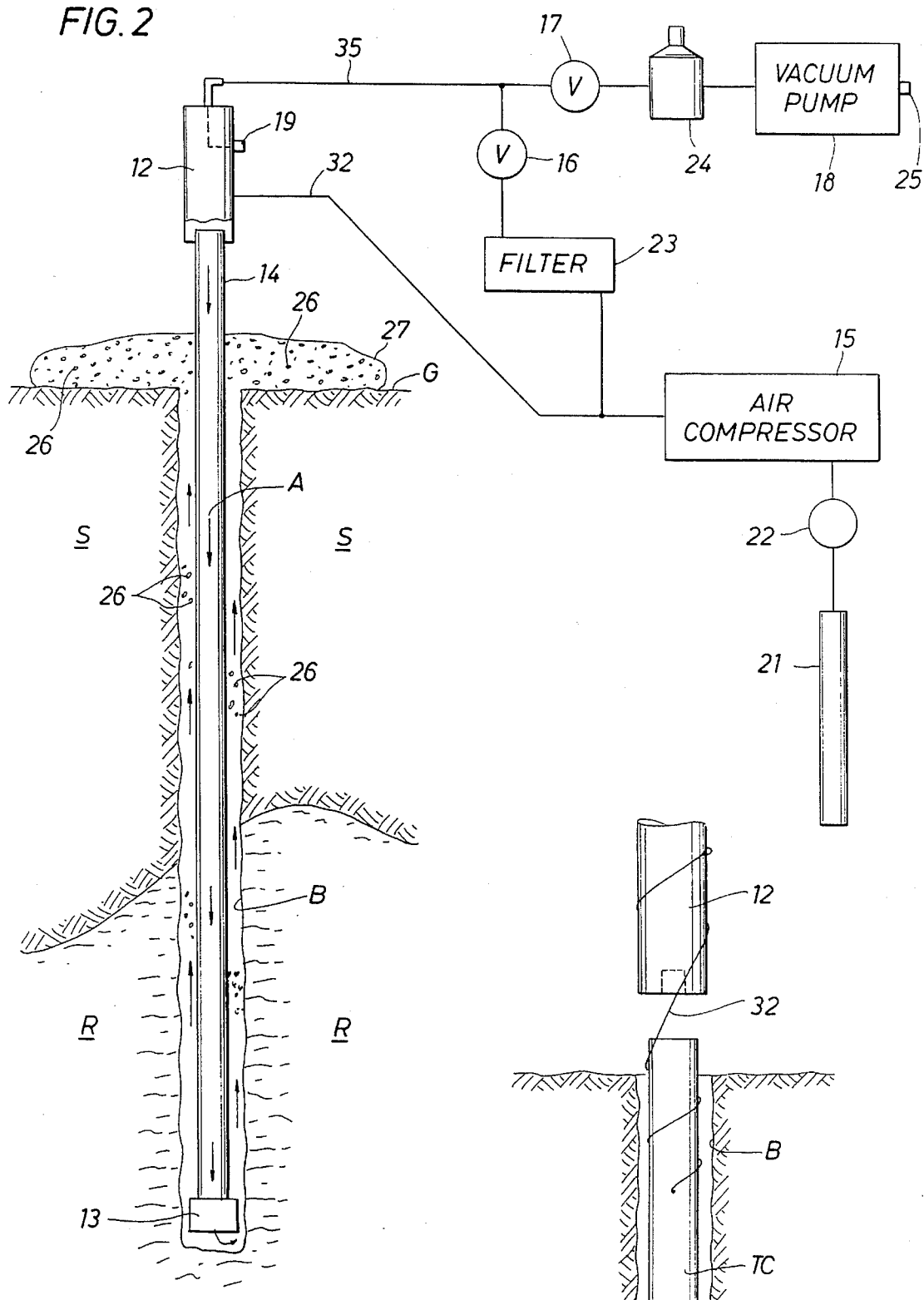

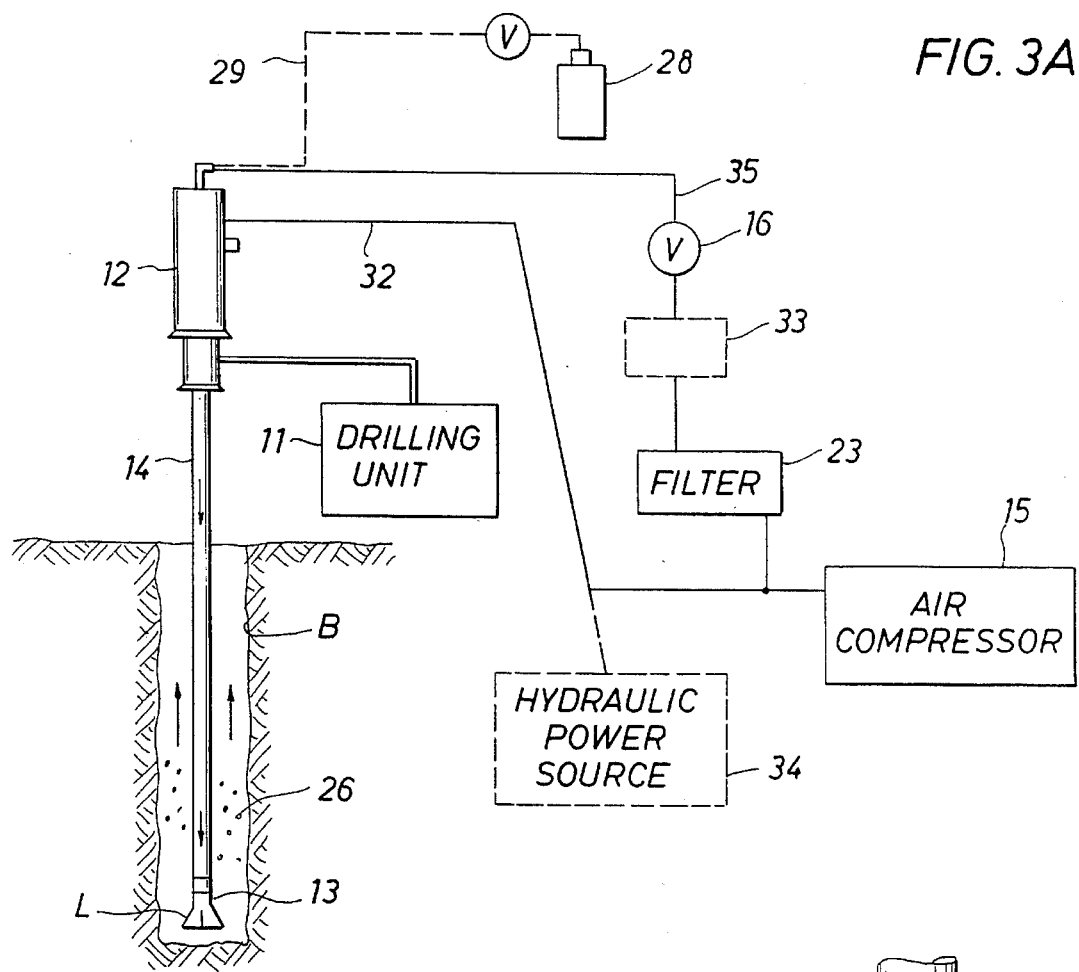
FIG. 3A
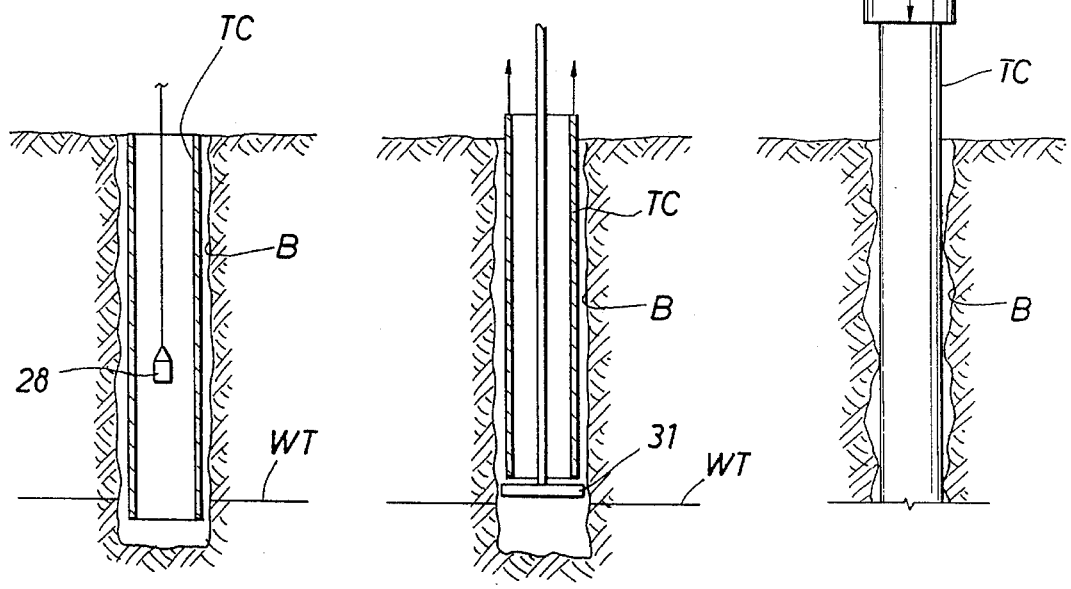
FIG. 3B
FIG. 3C
FIG. 3D 5,515,932

APPARATUS AND METHOD FOR ENVIRONMENTAL SURVEYING FOR CONTAMINANTS IN ALLUVIAL MATERIALS AND BEDROCK FORMATIONS

SPECIFICATION

This application forms a continuation in part of Applicants' previously filed U.S. application Ser. No. 08\126,907, filed Sep. 24, 1993, now U.S. Pat. No. 5,487,019 recently allowed to issue as amended.

BACKGROUND OF INVENTION

1. Field of Invention

This invention relates to method and apparatus for performing environmental surveys and prospecting for contaminants in alluvial materials and bedrock formations. More particularly, the invention relates to a system for the use of drilling apparatus and associated equipment for effective and efficient environmentally related drilling through both soil and bedrock, including setting and pulling casing, to enable sampling and analyzing soil vapors, collecting soil and water samples, completing ground water monitoring wells, installing and testing air sparging and vacuum extraction remediation apparatus through both soil and bedrock and testing for successful remediation.

2. Description of the Prior Art

The invention comprises an effective, efficient, and economical system for drilling in soil and bedrock, dealing with temporary casing and for in-situ sampling, testing, detection and/or for preparation for remediation of soil, bedrock, and ground water contamination. The system provides for the in situ collection of soil vapor, for the collection of soil and bedrock samples from discrete intervals and for the collection of ground water samples. The system facilitates the construction of temporary or permanent ground water monitoring wells for collecting ground water samples and in-situ air permeability testing. The system affords multiple site characterization techniques for investigating and remediating contaminated soils and ground water.

At locations where soil, bedrock, and/or ground water contamination occurs, it is often desirable to collect soil vapor data to determine the extent of vapor phase contamination. A monitoring system to sample soil vapor has enhanced effectiveness, efficiency, and economy if the same apparatus can be used to collect soil samples, ground water samples and to complete ground water monitoring wells, as the situation may require. It would also be desirable to have the above apparatus capable of installing and testing remediation equipment, including temporary casing. The system would have even further general application if the drilling mechanism were capable of boring through bedrock and consolidated formations as well as through alluvial materials and unconsolidated formations, and could unclog bit perforations without pulling the bit. Prior to this invention, environmentally related drilling systems have not been offered to provide this effective and efficient combination of field data collection and well completion techniques through both soil and bedrock.

Prior and present art soil vapor surveying techniques use hand drilling and hydraulic drilling. The industry has stayed away from pneumatic drilling with its concomitant circulating air systems because of a general belief that such pneumatic drilling would distort the soil vapor data. The present inventors, faced with a daunting task of environmental surveying through bedrock, experimented nonetheless with pneumatic drilling and circulating air systems, notwithstanding the negative reception it receives in the art. The inventors learned that, unexpectedly, an air balance is apparently achieved downhole. Air pressure and venturi effects may cancel each other out at the probe tip. Pneumatic drilling, thus it was discovered, can be used for environmental prospecting and it does not impermissibly dilute or destroy the soil vapors sampled, the significance of the vapor analysis data or other soil or water data.

In contrast to prior art soil vapor sampling machines and techniques, the present invention, through the use of rotary percussion drilling equipment, preferably pneumatic, is not only able to sample through bedrock but is also able to efficiently and effectively provide a technique capable of water sampling as well as soil sampling, and capable of the installation of ground water monitoring wells in both alluvial materials and bedrock formations. The subject invention provides the synergistic advantage of performing multiple field investigative tasks both in alluvial and bedrock subsurface environments. By performing soil vapor surveys, collecting soil and/or ground water samples for laboratory analysis, and installing ground water monitoring wells and remediation equipment in both bedrock and alluvial materials, the system qualifies uniquely to offer a range of field services not currently found in the trade. Some specific advantages of the system's drilling apparatus and techniques, including preferred embodiments, are that it uses conventional rock bits which allow a rapid drilling rate in both alluvial and bedrock environments. Rapid downhole techniques have been developed for blowing out clogged perforations that occur when running rock bits in certain soft soil. Consequently, site characterization and the remediation of contaminated sites can be achieved at a rapid pace, allowing the system to provide more information to land owners for a lesser cost than the alternative of using a combination of prior systems. Furthermore, the drill cuttings (contaminated wastes) produced by the drilling apparatus and technique are of substantially less volume than that produced by many other drilling techniques, thereby reducing contaminated soil disposal costs. Because of the drilling procedure utilized, the apparatus provides a cleaner bore hole wall than that offered by other drilling techniques. A cleaner bore hole wall allows any remediation system installed to become effective more quickly. The apparatus and system of the present invention is further unique in the trade in that in addition to investigative techniques, it can be utilized to both install and test air sparging/vacuum extraction remediation systems. Once the remediation equipment is installed (sparge or vacuum point), the machine may be used to inject air into the sparge pipes and measure air pressure responses in the bore hole located at varying distances from the air injection point. This data can then be used to determine the effective air permeability of soils/ bedrock for the efficient design of remediation systems, whether using air sparging/vacuum extraction independently or together. As cost control is becoming an increasingly important issue for environmental investigation and remediation, an apparatus and system that performs more efficiently and effectively both investigative and remediation tasks through a variety of subsurface environments is of enhanced value.

The invention further includes a method that is particularly adapted for testing water and soil during various phases of remediation and/or after remediation is deemed to be completed to confirm that contaminant concentrations have been reduced to levels within certain acceptable specifications. The prior art teaches the use of an hollow stem auger in such circumstances to drill test holes to determine if remediation is successful and complete. The auger drills to the water table to sample water and/or soil to confirm that the water or soil is clean. One benefit previously believed to adhere to the use of an auger was that the drilling itself was believed not to affect characteristics of the soil and water that needed to be tested. It was thought that pneumatic or hydraulic drilling would affect or destroy those characteristics, such as by using drilling fluids downhole as well as by using lubricants for the drill bit.

Several disadvantages of hollow stem auger drilling are obvious, namely, it is slow, inefficient and requires a large hole, approximately seven inches in diameter as opposed to two or three inches. But more recently discovered, for reasons presently unclear, the auger method also appears to lack its one perceived virtue, namely, not to affect important characteristics of the soil and/or water by the drilling process. Recent results from testing using prior art techniques after apparently successful remediation have appeared unrealistically negative. It is speculated that the cause may be that heat and pressure generated by the auger is vaporizing portions of the down-hole substances through pressure and friction. These vapors may migrate and contaminate adjacent soil and/or water.

Surprisingly, contrary to established expectations and the prevailing wisdom of the field, a rotary percussion drilling machine, preferably pneumatic, that circulates air or gas to remove the drill cuttings does not significantly appear to affect characteristics of the soil or water important to measure after remediation. Vaporizing of subsurface material is minimized using the rotary percussion drilling because the bit is cooled with circulating air or gas. Lubricants for the bit can be chosen that do not affect the results of the testing.

When testing subsequent to remediation, subsurface fluids, such as water, are not customarily lifted by vacuum pump. As there is no requirement to sample the soil and/or water while the drilling proceeds, a bore hole can be drilled directly to six inches or so below the water table, the drilling apparatus removed and the hole developed with temporary casing. Water is then lifted mechanically from the bottom of the hole, the casing pulled, and sample soil extracted from the hole, above or below the water table, using a device such as a split spoon sampler. The water and soil are subsequently tested for contaminants.

The present invention solves several difficulties that can be encountered when using a portable rotary percussion drilling machine for environmental surveying or prospecting. Perforations in the drill bit can become plugged when drilling through certain subsurface soils or materials, and difficulties can be encountered in certain subsurface formations in setting and removing temporary casing in a drilled borehole. The present invention includes method and apparatus for efficiently and effectively blowing out clogged perforations in the bit while drilling, and also includes adaptations to permit using the drilling machine itself to help set and remove casing.

SUMMARY OF THE INVENTION

The invention comprises apparatus and method for environmental surveying or prospecting for contaminants in alluvial materials and bedrock formations. The apparatus includes a portable rotary percussion drilling machine, possibly hydraulic but preferably pneumatic such that it uses one air compressor for powering the drilling and for providing air as gas circulation fluid. The machine utilizes a perforated rock drill bit and hollow stem drill rod.

The apparatus may include means for collecting cuttings from the air or gas circulation fluid and means for collecting fluids. The apparatus may include means for testing collected fluids and solids, as well as a soil and bedrock sampling tool and means for connecting the sampling tool to the drill rod. The apparatus may further include air sparging and vacuum extraction piping for installation into a drill bore hole and means for connecting the air compressor of the drilling machine to the installed piping. When the air compressor is connected to the piping, meters will be employed for monitoring air pressure and air flow rate in the piping downhole. In certain embodiments, means for measuring soil vapor concentration is connected to the exhaust of a vacuum pump and the drill rod is hexagonal.

Methods for environmental drilling, sampling and monitoring alluvial soil and bedrock include drilling a bore hole with a portable rotary percussion drilling machine using a perforated rock drill bit and hollow stem drill rod. Gas or air is circulated through the stem and bore hole as a circulation fluid, thereby displacing drill cuttings. A vacuum pump maybe connected to the hollow stem drill rod and underground fluid lifted by means of the pump through the bit and the rod without removing the drilling equipment. The extracted fluids may then be collected and analyzed, on site or in the labs. The method may include replacing the drill bit with a soil sampling tool and driving the tool to collect soil samples at a target depth. The method may further include withdrawing the drilling rod and machine from the bore hole and installing air sparging and vacuum extraction piping. A drilling machine compressor may then be connected to the piping and air or gas injected into the piping. Air or gas pressure and air or gas flow rate may then be monitored in order to understand the characteristics of the formation around the bore hole.

As a method for environmental sampling and monitoring alluvial soil and water subsequent to remediation efforts, the system includes drilling a bore hole to approximately water table height, or slightly below, using a portable rotary percussion drilling machine with a perforated rock drill bit and hollow stem drill rod. Preferably the machine is pneumatic, using the associated air compressor to provide circulation gas. Air or gas is circulated down the hollow stem and out the bore hole to displace drill cuttings. Preferably, the circulating gas is derived from an air compressor that powers a pneumatic hammer of the driver. The hole can be temporarily cased and water samples lifted from the hole and tested for contaminants. Subsequently, a portion of the casing may be pulled and samples of soil removed from the hole and also tested for contaminants. Alternately, of course the method may be used for sampling soil without sampling water or for sampling water without sampling soil.

The system also includes associated methods and apparatus for more efficient environmental prospecting, surveying and drilling for environmental purposes through alluvial soil to reach significant subsurface contaminant levels. These methods and apparatus include unclogging perforations in the rock bit that become clogged while drilling in certain soils by blowing them out without pulling the bit. Circulating compressed gas, or air, of at least 500 psi from a pressurized gas source down the hollow stem drill rod performs the function. Preferably, the pressurized gas source comprises a tank of nitrogen and supplies gas at 1000 psi, or 1500 psi. Use of a nonflammable, non-explosive inert gas is recommended. A circulating air source, may be also adapted to displace the drill cuttings, more particularly an air compressor associated with a pneumatic drill, by developing sufficient pressure in short bursts to blow out the clogged perforations.

The system may also include the capacity to temporarily case the hole by aid of the percussion hammer, driving the casing into the bore hole through an associated casing driving adaptor. Also, the percussion hammer, operating in reverse mode, may be used to aid pulling temporary casing from the hole by attaching a line between the hammer and the casing.

BRIEF DESCRIPTION OF THE DRAWINGS

FIG. 2 illustrates the operation of the system.

FIG. 3A–3E illustrate the operation of the system in general prospecting or surveying to sample soil and water after remediation, and including blowing clogged perforations and driving and pulling casing.

DETAILED DESCRIPTION OF THE PREFERRED EMBODIMENTS

Figure 1:
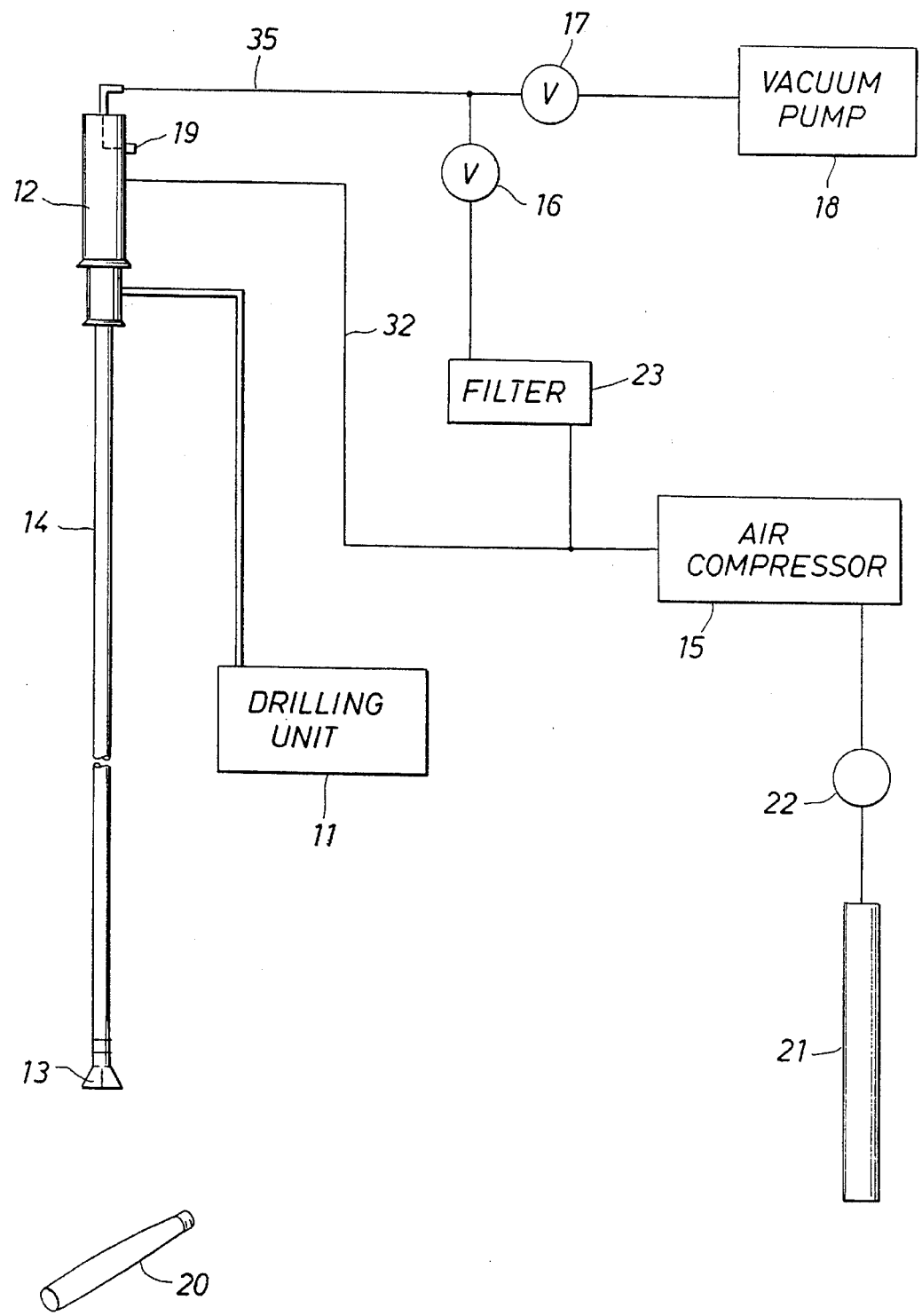
FIG. 1 illustrates the drilling machine and air compressor equipment.

In general, a drilling apparatus and method is disclosed for prospecting in soil and bedrock, sampling and analyzing soil vapors, collecting soil and water samples, completing ground water monitoring wells, and/or installing and testing air sparging/vacuum extraction remediation systems which can be utilized to survey through alluvial soil S and bedrock R, as illustrated in FIG. 2. In operation a portable rotary percussion drilling machine, preferably pneumatic, including driver 12 having a percussion hammer, drives a drill bit through the soil S, bedrock R, and/or alluvial materials to be prospected for vapor phase, soil, bedrock, and/or ground water contamination. Gas or air A, as a circulation fluid, is injected down the hollow stem of the drill rod 14 and through the perforated drill bit 13. The circulation gas A displaces drill cuttings 26 from the boring B which are collected at the surface on plastic sheet 27. Once the drill bit reaches a target depth, the gas source for cleaning out the boring is disconnected and a vacuum pump 18 is connected to the hollow stem of the drill rod. Suitable means for connecting the pump can be devised, given the selection of a particular size and style of pump and a particular size and style of driver. The means may include a valve 17 and a vessel 24 for collecting water samples. The vacuum pump extracts vapors from the soil or bedrock through the hollow drill rod and the perforated drill bit, the bit being sometimes referred to in this function as the probe tip. The vapors may then be field screened for vapor concentration, using equipment known in the art, and/or collected for analysis. Both operations may be performed at the exhaust 25 of pump 18. If desired, the probe tip and hollow drill rod may also be used to vacuum water samples from the formation for laboratory analysis.

As the drill bit approaches the target depth, if the bit is in alluvial materials, the air or gas may be turned off, the drill stopped, and the drill physically pushed for the last inch or so. If the target depth lies within bedrock, the above technique is not possible, but also it is not important.

After vapor and/or ground water collection is complete, the vacuum pump is disconnected. At this point the drill rod and bit may be withdrawn from the bore hole and the bit replaced by a soil/bedrock sampling tool 20. Given the size and style of drill rod selected and the type of soil sampling tool, specific means can be devised to connect the tool to the drill rod. The rod and tool is then placed back into the bore hole and the soil or bedrock sampled by driving the tool, which may be a split spoon sampler, into the target horizon. The rod and tool are subsequently withdrawn from the bore hole and the soil sample is collected. The rod and rock bit are then placed back into the bore hole, the driver reconnected, and the process is repeated.

Once the lowest target depth is achieved, usually by 40 or 50 feet, and if contamination is confirmed, air-sparging and/or vacuum extraction piping 21 may be installed in the bore hole in preparation for remediation. All downhole rods are withdrawn from the boring and the drilling mechanism may be utilized, if or when necessary, to facilitate installing the piping. Subsequent to installation, an air compressor, if used to drive the drilling mechanism may be connected to the sparge/vacuum pipe and air injected into the piping. Air or gas pressure and flow rate data may be monitored at the injection point and at locations of varying distances from the injection point to be used to determine the effective air or gas permeability of the soils/bedrock. This data enables the more efficient design of a remediation system which may use air sparging/vacuum extraction independently or together.

More particularly in reference to a preferred embodiment of the equipment, FIG. 1 shows a pneumatic driver 12, controlled by means of drilling unit 11 and utilizing air compressor 15 through connection 32 to pneumatically drive a perforated rock drill bit 13 into soil, bedrock, and/or alluvial materials to be prospected for vapor phase, soil, bedrock, and/or ground water contamination. The drilling mechanism effects a percussion drilling with some rotation. Air from the compressor 15 is filtered by filter 23 to limit the introduction of contaminants, such as hydrocarbons and is connected to driver 12 through line 35 to provide circulation fluid.

The equipment illustrated in FIG. 1 can be loaded on a fifteen foot long flatbed truck. Drilling unit 11 controls driver 12 and compressed air source 15. In one preferred embodiment, pneumatic driver 12 is of a type that is the standard driver for Ingersoll-Rand wagon or air track drills and is similar to an Ingersoll-Rand YD90 Drifter. A suitable driver can be purchased from Ingersoll-Rand and will be approximately two feet long and up to one foot in diameter. Such driver is suitable for penetrating depths shallower than five hundred feet, which covers the region of interest for environmental surveys. A suitable compressed air source would be an Ingersoll-Rand 250 cfm (cubic feet per minute) air compressor or larger. Suitable air filters can be purchased from W. W. Grainger, Inc. Rock bit 13 is a standard rock bit with diameter ranging from 1.75 to 4.0 inches and can be purchased from IMSCO, Inc.

Air from compressor 15 not only powers the pneumatic driver but is also injected, through valve 16 and through connection with driver 12 through line 35, down the hollow stem of the drill rod 14 and through perforated rock drill bit 13. The air circulation fluid A displaces drill cuttings 26 from the boring B. These cuttings 26 are carried to the surface and collected on a plastic sheet 27 in the preferred embodiment, as shown in FIG. 2. The hollow drill rod 14 is preferably of one inch to 1.5 inches in diameter and hexagonal in cross-section.

Once the drill bit reaches a target depth, the air compressor source 15 for drilling and cleaning out the boring can be disconnected and vacuum pump 18 connected through valve 17 to driver 12 and hollow stem drill rod 14. Vacuum pump 18 extracts vapors from the soil or bedrock through the perforated rock drill bit, operating as a probe tip, and through the hollow rod. The vapors may be collected and/or metered at the pump exhaust 25. The vapors are field screened for vapor concentration and/or saved for analysis. If desired, the probe tip and hollow stem drill rod can also be used to vacuum water samples from the formation for laboratory analysis. The water samples may be collected in vessel 24 located in the line communicating the vacuum pump with the driller. If soil vapor only is collected, vessel 24 is removed from the vacuum line.

The vacuum pump used to extract soil vapor and/or ground water samples in the preferred embodiment is similar to a Dayton No. 4Z336 one-half HP (horsepower) vacuum pump which can be purchased from W. W. Grainger, Inc.

After vapor and/or ground water collection is complete, vacuum pump 18 is disconnected. At this point hollow drill rod 14 and rock bit 13 may be withdrawn from the bore hole and the rock bit replaced by soil/bedrock sampling tool 20. The soil/bedrock sampling tool can be a standard 2" o.d. split spoon sampler which can be purchased from Mills Machine Shop. The drill rod is then placed back into the bore hole and the soil or bedrock sampled by pneumatically driving, using driving mechanism 12, soil sampling tool 20 into the target horizon. Drill rod 14 and soil sampling tool 20 are then withdrawn and the soil sample is collected. The drill rod 14 and rock bit 13 are placed back into the bore hole, the pneumatic driver reconnected, and the process is repeated.

Once the lowest target depth is achieved all downhole equipment is withdrawn from the bore hole. If contamination is confirmed, air-sparging and/or vacuum extraction piping 21, shown only illustratively in FIGS. 1 and 2, may be installed in the bore hole in preparation for commencing remediation.

The typical air sparge/vacuum extraction piping is PVC pipe. To install 2" PVC piping, a 3" bore hole is drilled and the pipe then placed down the bore hole. If the bore hole caves, free fall emplacement of the piping is not possible. In this situation, the piping may be installed by using the pneumatic driver to drive the pipe into the wall. At this point air compressor 15 may be connected to the installed sparge/vacuum pipe, utilizing some connection device suitable for the size of piping and the compressor hose, and air injected into the piping. The sparge/vacuum connectors would be designed based on hose size and the outlet provided by the piping used. The air pressure and flow rate may be monitored utilizing air flow meters 22 placed at the injection point and at boring depths located varying distances from the injection point. The air flow meters can be a type similar to 4" 2 magnehelic differential pressure gauges and can be purchased from W. W. Grainger, Inc. This data is then used to determine the effective air permeability of the soils/bedrock for a more efficient design of a remediation system which uses air sparging/vacuum extraction independently or together.

When it is desired to test soil and water for contaminants subsequent to remediation efforts, as illustrated in FIGS. 3A, 3B and 3D, a portable rotary percussion drilling machine can be used, preferably pneumatic, to drive a drill bit through the soil S (and bedrock R, if any). Gas or air A, as a circulation fluid, is injected down the hollow stem of the drill rod 14 and through the perforated drill bit 13 to displace the cuttings. Conceivably the circulation fluid could be piped down a separate tube along the side of the drill rod and communicated to the rock bit. Using the hollow stem drill rod for this purpose offers convenience and efficiency. Preferably the drilling machine is pneumatically driven, using an air compressor to provide drilling power and circulation fluid.

However, as an alternate embodiment, it would be possible to use a hydraulic rock drill machine with a separate source of gas or air as the circulation fluid. In FIG. 3A, box 34 represents an alternative source of hydraulic power, such as an oil based source, that communicates through line 32 with driver 12 to power the driver. Air compressor 15 is shown as the preferred pneumatic source of drive through connection line 35. Air compressor 15, or an alternate source of pressurized gas, such as illustrated by tank 28, should be used to supply circulation fluid to the drill rod. Hydraulic oil could not be used as circulation fluid A.

The circulation gas or air A displaces drill cuttings 26 from the boring B. Once the drill bit reaches the target depth, which should be a few inches below the water table level, the drilling machine rod and bit are removed from the bore hole. The hole is usually temporarily cased with casing TC. Any suitable mechanism may be lowered through the temporarily cased hole to remove a sample of water for testing, as illustrated in FIG. 3B. If a soil sample is desired, the temporary casing may be slightly pulled and a sample of soil selected, such as with suitable apparatus 31, as illustrated in FIG. 3D.

FIGS. 3A through 3E illustrate more particular uses of the above apparatus for environmental surveying and prospecting. FIG. 3A illustrates drill bit 13 attached to hollow stem drill rod 14, the rod being powered by driver 12 which is controlled by means of drilling unit 11 and powered in turn by air compressor 15 (or hydraulic fluid source 34) connected in known manners. The bit is hydraulically or pneumatically driven into the soil and bedrock to reach a significant contaminant level. To test for a successful prior remediation of ground water, for instance, the bit would be driven down to a level that is a few inches below water table level WT. A source of gas, such as air compressor 15, may be utilized to dispense drill cuttings by circulating the gas down the drill rod. Such air preferably may be siphoned off from an air compressor 15 used to power the driver, filtered and routed through the pneumatic driller to reach the drill rod, as described above. Other sources of pressurized gas such as tank 28 could also be used to supply circulation fluid to the drill rod.

During drilling, especially in some subsurface materials and soils, the perforations or air holes in the rock bit may become clogged with a fine-grained subsurface material. This may diminish the ability of the circulating gas to clean out the borehole. It also may not allow sufficient vapor flow to obtain a representative soil vapor samples. It is desirable to clean out such clogged tips downhole rather than to remove the drill rod and bit out of the hole, to minimize the loss of valuable time. The invention includes method and apparatus to clean out such holes in the perforated bit downhole, utilizing a source of gas pressurized to at least 500 psi. Preferably the source of gas comprises a tank of pressurized nonflammable, nonexplosive inert gas 28, such as nitrogen, and is pressurized to 1000 psi, or 1500 psi. Alternatively, an air compressor 15 driving the pneumatic hammer could be adapted to provide a source of short bursts of sufficiently high pressure gas. Although such air compressors typically deliver a maximum of 120 psi for driving the percussion machine, adaptions can be designed to develop short spurts of very high pressure air.

In the illustrated embodiment, nitrogen tank 28 is shown releasably connected to the drill rod through driver 12, similar to the manner in which air compressor 15 is connected to provide circulation fluid through driver 12. When the tank valve is opened, the pressurized gas is injected through the circulation air channel and into the hollow stem drill rod. Due to its high pressure, the gas has been shown to be capable of cleaning out clogged air holes of a rock bit while the bit remains in the ground. Nitrogen tank 28 may be releasably connected by line 29 to driller 12 using suitable fittings and valves. Alternately, adaptor 23 is shown installed in circulation air line 32 between the filter and the driver. Adaptor 23 may use air compressor 15 to develop a sufficient source of highly pressurized bursts of air, at least 500 psi, for blowing out the bit holes.

When checking for successful remediation, subsequent to reaching the water table or other desired level, the drilling equipment is frequently removed from bore hole B and temporary casing TC installed. For installation of well casing, if downhole conditions inhibit simple freefall of the casing, as illustrated in FIG. 3C, the invention includes using a casing driving adaptor AD to be affixed or located between the driver hammer and the casing. Adapter AD may comprise a short length of pipe that fits over the top of casing TC, the pipe having a plate and a rod attached to its top where the rod is structured to fit into the percussion hammer in place of the drill rod and/or its adaptor linkage. By use of such arrangement the casing can be driven by driver 12 into the borehole using the percussion drilling machine. Again, subsequent to the installation of the casing, a variety of known means for lifting water out of the bottom of the bore hole could utilized to sample the water, as illustrated in FIG. 3B. And if desired, temporary casing TC can be pulled slightly and a sample of the soil taken, as in FIG. 3D.

For removing temporary casing, FIG. 3E, as after completion of groundwater sampling, a pulling device or line 32, such as a cable or chain, can be attached between temporary casing TC and the percussion hammer portion of driver 12, operated in a reverse mode, (or alternately a separate extractor, not shown). This facilitates upward extraction of the well casing.

Having described the invention above, various modifications of the techniques, procedures, material and equipment will be apparent to those in the art. It is intended that all such variations within the scope and spirit of the appended claims be embraced thereby. While specific embodiments and features of the invention have been disclosed herein, it will be readily understood that the invention encompasses all enhancements and modifications within the scope and spirit of the following claims.

What is claimed is:

1. A method for environmental sampling and monitoring in alluvial soil and bedrock comprising:

drilling a bore hole to approximately water table height with a portable rotary percussion drilling machine using a perforated rock drill bit and hollow stem drill rod;

circulating gas down the hollow stem and out the bore hole to displace drill cuttings;

temporarily casing the hole;

lifting a water sample from the hole; and testing the water sample for contaminants.

2. The method for claim 1 that further includes pulling a portion of the casing; removing a sample of the soil from the bore hole; and testing the soil for contaminants.

3. A method for environmental sampling and monitoring in alluvial soil and bedrock comprising:

drilling a bore hole with a portable rotary percussion drilling machine having a perforated rock drill bit and hollow stem drill rod;

circulating gas down the hollow stem and out the bore hole to displace drilling cuttings;

removing a sample of the soil from the bore hole; and testing the soil for contaminants.

4. A drilling method for environmental prospecting comprising:

drilling a bore hole to a potential subsurface contaminant level using a portable rotary percussion drilling machine having a perforated rock drill bit and hollow stem drill rod;

circulating gas down the stem and out the bore hole to displace drill cuttings; and blowing compressed gas from at least a 500 psi pressurized gas source down the drill rod to dislodge a clogged perforation in the bit.

5. The method of claim 4 wherein the gas source comprises a tank of nitrogen.

6. A drilling method for environmental prospecting comprising:

drilling a bore hole to a potential subsurface contaminant level using a portable rotary percussion drilling machine having a percussion hammer, a perforated rock drill bit and hollow stem drill rod;

circulating gas down the stem and out the bore hole to displace drill cuttings; and temporarily casing the hole by driving the casing into the bore hole using a casing driving adapter located between the casing and percussion hammer.

7. The method of claim 6 that includes pulling the temporary casing by attaching a line between the casing and the percussion hammer and operating the hammer in a reverse mode.

8. The method of claims 1, 3, 4 or 6 wherein the machine comprises a pneumatic machine and an air compressor supplies pneumatic drive and circulation gas.

9. Apparatus for environmental surveying for contaminants in alluvial materials and bedrock formations comprising:

a portable rotary percussion drilling machine having a rotary percussion driver, hollow stem drill rod connected to the driver to transmit rotary percussion motion, and a perforated rock drill bit connected to the drill rod;

a source of at least 500 psi pressurized gas; and means for connecting the source of pressurized gas to the hollow stem of the drill rod such that pressurized gas is communicated through the hollow stem.

10. The apparatus of claim 9 wherein the source of pressurized gas comprises a nitrogen tank.

11. The apparatus of claim 9 wherein the driver comprises a pneumatic driver, the source of pressurized gas includes an air compressor used to power the pneumatic driver, and including means for adapting the air compressor to provide at least 500 psi pressurized gas.

12. The apparatus of claim 9 that includes a source of circulation gas connected to the driver for fluid communication with the drill rod to circulate gas down the hollow stem and out the borehole to displace drilling cuttings.

13. The apparatus of claim 9 wherein the driver comprises a pneumatic driver having an air compressor and said air compressor comprises the source circulation gas.

14. Apparatus for environmental surveying for contaminants in alluvial materials and bedrock formations comprising:

a portable rotary percussion drilling machine having a rotary percussion driver, hollow stem drill rod connected to the driver to transmit rotary percussion motion, and a perforated rock drill bit connected to the drill rod;

an air compressor connected to the driver such that compressed air is communicated through the hollow stem; and an adaptor releasably attachable between the driver and temporary casing for transmitting driving force from the percussion driver to the casing.

15. Apparatus for environmental surveying for contaminants in alluvial materials and bed rock formations comprising:

a portable rotary percussion drilling machine having a rotary percussion driver, hollow stem drill rod connected to the driver to transmit rotary percussion motion, and a perforated rock drill bit connected to drill rod;

an air compressor connected to the driver such that compressed air is communicated through the hollow stem;

temporary casing;

a line;

means for connecting the line to the temporary casing; and means for connecting the line to the rotary percussion driver.

16. The apparatus of claim 14 or 15 wherein the machine comprises a pneumatic machine and the air compressor is connected to the driver to provide pneumatic drive.

* * * * *